US 11,903,996 B2

United States Patent
Fritzinger et al.

(10) Patent No.: US 11,903,996 B2
(45) Date of Patent: Feb. 20, 2024

(54) MODULATORS OF COMPLEMENT FUNCTION

(71) Applicants: David C. Fritzinger, Monroe, NJ (US); Daniel E. Benjamin, Millstone Township, NJ (US)

(72) Inventors: David C. Fritzinger, Monroe, NJ (US); Daniel E. Benjamin, Millstone Township, NJ (US)

( * ) Notice: Subject to any disclaimer, the term of this patent is extended or adjusted under 35 U.S.C. 154(b) by 1429 days.

(21) Appl. No.: 15/288,830

(22) Filed: Oct. 7, 2016

(65) Prior Publication Data
US 2018/0369328 A1 Dec. 27, 2018

Related U.S. Application Data

(60) Provisional application No. 62/238,512, filed on Oct. 7, 2015.

(51) Int. Cl.
| | | |
|---|---|---|
| *A61K 38/17* | (2006.01) | |
| *C07K 14/47* | (2006.01) | |
| *A61P 37/04* | (2006.01) | |
| *A61K 47/10* | (2017.01) | |
| *C12N 15/62* | (2006.01) | |
| *C12N 15/79* | (2006.01) | |
| *C12N 9/64* | (2006.01) | |
| *A61K 38/00* | (2006.01) | |
| *C07K 14/015* | (2006.01) | |

(52) U.S. Cl.
CPC .......... *A61K 38/1725* (2013.01); *A61K 47/10* (2013.01); *A61P 37/04* (2018.01); *C07K 14/015* (2013.01); *C07K 14/47* (2013.01); *C07K 14/472* (2013.01); *C12N 15/62* (2013.01); *C12N 15/79* (2013.01); *A61K 38/00* (2013.01); *C12N 9/64* (2013.01); *Y02A 50/30* (2018.01)

(58) Field of Classification Search
None
See application file for complete search history.

(56) References Cited

PUBLICATIONS

Hew et al. Identification of functionally important amino acid sequences in cobra venom factor using human C3/Cobra venom factor hybrid proteins.' Toxicon 167:106-116, 2019.*
Misumi et al. Nucleotide and deduced amino acid sequence of rat complement C3. Nucleic Acids Res. 18(8):2178, 1990.*
Campbell et al. 'Monoclonal Antibody Technology.', edited by R. H. Burdon, Elsevier, 1987, pp. 29-30.*
Harlow et al. 'Antibodies a Laboratory Manual.' Cold Spring Harbor, New York. Cold Spring Harbor Press: 141-157, 1988.*
Fujita, Evolution of the lectin-complement pathway and its role in innate immunity. Nat Rev Immunol2.
Gros et al., Complement driven by conformational changes. Nat Rev Immunol8, 48-58 (2008).
Ji et al., Ancient origin of the complement lectin pathway . . . , Proc. Natl. Acad. Sci. USA94, 6340-6345 (1997).
Walport, N Engl J Med344, 1058-1066 (2001).
Walport, N Engl J Med344, 1140-1144 (2001).
Pangburn, Initiation of the alternative complement pathway due to spontaneous hydrolysis of the thioester of C3. Annals of the New York Academy of Sciences421, 291-298 (1983).
Vogel et al., Cobra venom factor: improved method for purification and biochemical characterization. Journal of Immunological Methods73, 203-220 (1984).
Janssen et al., Insights into complement convertase formation based on the structure of the factor B-cobra venom factor complex. The EMBO Journal 28, 2469-2478 (2009).
Rooijakkers, Structural and functional implications of the alternative complement pathway C3 convertase stabilized by a *Staphylococcal* inhibitor. Nat Immunol10, 721-727 (2009).
O'Keefe et al., A novel cleavage product of human complement component C3 with structural and functional properties of cobra venom factor. J. Biol. Chem.263, 12690-12697 (1988).
Cochrane et al., Depletion of plasma complement in vivo by a protein of cobra venom: its effect on various immunologic reactions. J. Immunol. 105, 55-69 (1970).
Fritzinger et al., Functional characterization of human C3/cobra venom factor hybrid proteins for therapeutic . . . Developmental & Comparative Immunology33, 105-116 (2009).
Wu et al., Structure of complement fragment C3b-factor H and implications for host protection by complement regulators. Nat Immunol10, 728-733 (2009).

(Continued)

*Primary Examiner* — Nora M Rooney

(57) ABSTRACT

The invention relates generally to a modified human C3 protein containing a number of single amino acid changes in the α and β-chain of human C3 protein, designed to increase the affinity of the modified protein to factor B or Bb, to decrease the affinity of the modified protein to factor H, and to reduce the immunogenicity of the modified protein as compared to the native human C3 protein, a nucleotide sequence encoding the modified C3 protein, a plasmid or viral vector containing the nucleotide sequence for expression the modified C3 protein, and a host cell containing the plasmid or viral vector. We also present a polyethylene glycol covalently bound to the modified C3 protein for reducing immunogenicity and increasing plasma half-life of the modified C3 protein; a method for depleting complement in a patient by administering the modified C3 protein to the patient in an amount effective to deplete complement; a method of ameliorating effects caused by or disease or a method of ameliorating reperfusion injury in a patient by delivering the modified C3 protein.

16 Claims, 8 Drawing Sheets

Specification includes a Sequence Listing.

(56) References Cited

PUBLICATIONS

Kajander et al., Dual interaction of factor H with C3d and glycosaminoglycans in host-nonhost . . . Proceedings of the National Academy of Sciences 108, 2897-2902 (2011).

Chen et al., High-efficiency transformation of mammalian cells by plasmid DNA. Mol. Cell. Biol. 7, 2745-2752 (1987).

Dalby et al., Advanced transfection with Lipofactamine 2000 reagent: primary neurons, siRNA and highthrouhput applications. Science Direct, Methods 33 (2004).

Boels et al., Identification and characterisation of GPR100 as a novel human G protein-coupled bradykinin receptor. Br J Pharmacology 140, 932-938 (2003).

\* cited by examiner

Modulators of complement function List of Sequences: Figure 1A (SEQID1) ProC3 sequence:

```
Sequence: Pro_human_C3 Range: 1 to 1642

20                    40                    60
        GSPMYSIITPNILRLESEETMVLEAHDAQGDVPVTVTVHDFPGKKLVLSSEKTVLTPATN 80                   100                   120
        HMGNVTFTIPANREFKSEKGRNKFVTVQATFGTQVVEKVVLVSLQSGYLFIQTDKTIYTP 140                   160                   180
        GSTVLYRIFTVNHKLLPVGRTVMVNIENPEGIPVKQDSLSSQNQLGVLPLSWDIPELVNM 200                   220                   240
        GQWKIRAYYENSPQQVFSTEFEVKEYVLPSFEVIVEPTEKFYYIYNEKGLEVTITARFLY 260                   280                   300
        GKKVEGTAFVIFGIQDGEQRISLPESLKRIPIEDGSGEVVLSRKVLLDGVQNLRAEDLVG 320                   340                   360
        KSLYVSATVILHSGSDMVQAERSGIPIVTSPYQIHFTKTPKYFKPGMPFDLMVFVTNPDG 380                   400                   420
        SPAYRVPVAVQGEDTVQSLTQGDGVAKLSINTHPSQKPLSITVRTKKQELSEAEQATRTM 440                   460                   480
        QALPYSTVGNSNNYLHLSVLRTELRPGETLNVNFLLRMDRAHEAKIRYYTYLIMNKGRLL 500                   520                   540
        KAGRQVREPGQDLVVLPLSITTDFIPSFRLVAYYTLIGASGQREVVADSVWVDVKDSCVG 560                   580                   600
        SLVVKSGQSEDRQPVPGQQMTLKIEGDHGARVVLVAVDKGVFVLNKKNKLTQSKIWDVVE 620                   640                   660
        KADIGCTPGSGKDYAGVFSDAGLTFTSSSGQQTAQRAELQCPQPAARRRSVQLTEKRMD 680                   700                   720
        KVGKYPKELRKCCEDGMRENPMRFSCQRRTRFISLGEACKKVFLDCCNYITELRRQHARA 740                   760                   780
        SHLGLARSNLDEDIIAEENIVSRSEFPESWLWNVEDLKEPPKNGISTKLMNIFLKDSITT 800                   820                   840
        WEILAVSMSDKKGICVADPFEVTVMQDFFIDLRLPYSVVRNEQVEIRAVLYNYRQNQELK 860                   880                   900
        VRVELLHNPAFCSLATTKRRHQQTVTIPPKSSLSVPYVIVPLKTGLQEVEVKAAVYHHFI 920                   940                   960
        SDGVRKSLKVVPEGIRMNKTVAVRTLDPERLGREGVQKEDIPPADLSDQVPDTESETRIL 980                  1000                  1020
        LQGTPVAQMTEDAVDAERLKHLIVTPSGCGEQNMIGMTPTVIAVHYLDETEQWEKFGLEK
```

Figure 1B Continuation of (SEQID1) ProC3 sequence:

```
          1040                1060                1080
RQGALELIKKGYTQQLAFRQPSSAFAAFVKRAPSTWLTAYVVKVFSLAVNLIAIDSQVLC 1100                1120                1140
GAVKWLILEKQKPDGVFQEDAPVIHQEMIGGLRNNNEKDMALTAFVLISLQEAKDICEEQ 1160                1180                1200
VNSLPGSITKAGDFLEANYMNLQRSYTVAIAGYALAQMGRLKGPLLNKFLTTAKDKNRWE 1220                1240                1260
DPGKQLYNVEATSYALLALLQLKDFDFVPPVVRWLNEQRYYGGGYGSTQATFMVFQALAQ 1280                1300                1320
YQKDAPDHQELNLDVSLQLPSRSSKITHRIHWESASLLRSEETKENEGFTVTAEGKGQGT 1340                1360                1380
LSVVTMYHAKAKDQLTCNKFDLKVTIKPAPETEKRPQDAKNTMILEICTRYRGDQDATMS 1400                1420                1440
ILDISMMTGFAPDTDDLKQLANGVDRYISKYELDKAFSDRNTLIIYLDKVSHSEDDCLAF 1460                1480                1500
KVHQYFNVELIQPGAVKVYAYYNLEESCTRFYHPEKEDGKLNKLCRDELCRCAEENCFIQ 1520                1540                1560
KSDDKVTLEERLDKACEPGVDYVYKTRLVKVQLSNDFDEYIMAIEQTIKSGSDEVQVGQQ 1580                1600                1620
RTFISPIKCREALKLEEKKHYLMWGLSSDFWGEKPNLSYIIGKDTWVEHWPEEDECQDEE

1640
NQKQCQDLGAFTESMVVFGCPN
```

Figure 2A (SEQID2) ProC3 DNA/RNA sequence

```
                  20                      40                      60
AGTCCCATGTACTCTATCATCACCCCCAACATCTTGCGGCTGGAGAGCGAGGAGACCATG 80                     100                     120
GTGCTGGAGGCCCACGACGCGCAAGGGGATGTTCCAGTCACTGTTACTGTCCACGACTTC 140                     160                     180
CCAGGCAAAAAACTAGTGCTGTCCAGTGAGAAGACTGTGCTGACCCCTGCCACCAACCAC 200                     220                     240
ATGGGCAACGTCACCTTCACGATCCCAGCCAACAGGGAGTTCAAGTCAGAAAAGGGGCGC 260                     280                     300
AACAAGTTCGTGACCGTGCAGGCCACCTTCGGGACCCAAGTGGTGGAGAAGGTGGTGCTG 320                     340                     360
GTCAGCCTGCAGAGCGGGTACCTCTTCATCCAGACAGACAAGACCATCTACACCCCTGGC 380                     400                     420
TCCACAGTTCTCTATCGGATCTTCACCGTCAACCACAAGCTGCTACCCGTGGGCCGGACG 440                     460                     480
GTCATGGTCAACATTGAGAACCCGGAAGGCATCCCGGTCAAGCAGGACTCCTTGTCTTCT 500                     520                     540
CAGAACCAGCTTGGCGTCTTGCCCTTGTCTTGGACATTCCGGAACTCGTCAACATGGGC 560                     580                     600
CAGTGGAAGATCCGAGCCTACTATGAAAACTCACCACAGCAGGTCTTCTCCACTGAGTTT 620                     640                     660
GAGGTGAAGGAGTACGTGCTGCCCAGTTTCGAGGTCATAGTGGAGCCTACAGAGAAATTC 680                     700                     720
TACTACATCTATAACGAGAAGGGCCTGGAGGTCACCATCACCGCCAGGTTCCTCTACGGG 740                     760                     780
AAGAAAGTGGAGGGAACTGCCTTTGTCATCTTCGGGATCCAGGATGGCGAACAGAGGATT 800                     820                     840
TCCCTGCCTGAATCCCTCAAGCGCATTCCGATTGAGGATGGCTCGGGGAGGTTGTGCTG 860                     880                     900
AGCCGGAAGGTACTGCTGGACGGGGTGCAGAACCTCCGAGCAGAAGACCTGGTGGGGAAG 920                     940                     960
TCTTTGTACGTGTCTGCCACCGTCATCTTGCACTCAGGCAGTGACATGGTGCAGGCAGAG 980                    1000                    1020
```

Figure 2B Continuation of (SEQID2) ProC3 DNA/RNA sequence

CGCAGCGGGATCCCCATCGTGACCTCTCCCTACCAGATCCACTTCACCAAGACACCCAAG

```
              1040              1060              1080
TACTTCAAACCAGGAATGCCCTTTGACCTCATGGTGTTCGTGACGAACCCTGATGGCTCT 1100              1120              1140
CCAGCCTACCGAGTCCCCGTGGCAGTCCAGGGCGAGGACACTGTGCAGTCTCTAACCCAG 1160              1180              1200
GGAGATGGCGTGGCCAAACTCAGCATCAACACACACCCCAGCCAGAAGCCCTTGAGCATC 1220              1240              1260
ACGGTGCGCACGAAGAAGCAGGAGCTCTCGGAGGCAGAGCAGGCTACCAGGACCATGCAG 1280              1300              1320
GCTCTGCCCTACAGCACCGTGGGCAACTCCAACAATTACCTGCATCTCTCAGTGCTACGT 1340              1360              1380
ACAGAGCTCAGACCCGGGGAGACCCTCAACGTCAACTTCCTCCTGCGAATGGACCGCGCC 1400              1420              1440
CACGAGGCCAAGATCCGCTACTACACCTACCTGATCATGAACAAGGGCAGGCTGTTGAAG 1460              1480              1500
GCGGGACGCCAGGTGCGAGAGCCCGGCCAGGACCTGGTGGTGCTGCCCCTGTCCATCACC 1520              1540              1560
ACCGACTTCATCCCTTCCTTCCGCCTGGTGGCGTACTACACGCTGATCGGTGCCAGCGGC 1580              1600              1620
CAGAGGGAGGTGGTGGCCGACTCCGTGTGGGTGGACGTCAAGGACTCCTGCGTGGGCTCG 1640              1660              1680
CTGGTGGTAAAAAGCGGCCAGTCAGAAGACCGGCAGCCTGTACCTGGGCAGCAGATGACC 1700              1720              1740
CTGAAGATAGAGGGTGACCACGGGGCCCGGGTGGTACTGGTGGCCGTGGACAAGGGCGTG 1760              1780              1800
TTCGTGCTGAATAAGAAGAACAAACTGACGCAGAGTAAGATCTGGGACGTGGTGGAGAAG 1820              1840              1860
GCAGACATCGGCTGCACCCCGGGCAGTGGGAAGGATTACGCCGGTGTCTTCTCCGACGCA 1880              1900              1920
GGGCTGACCTTCACGAGCAGCAGTGGCCAGCAGACCGCCCAGAGGGCAGAACTTCAGTGC 1940              1960              1980
CCGCAGCCAGCCGCCCGCCGACGCCGTTCCGTGCAGCTCACGGAGAAGCGAATGGACAAA
```

Figure 2C Continuation of (SEQID2) ProC3 DNA/RNA sequence

```
                2000                2020                2040
       GTCGGCAAGTACCCCAAGGAGCTGCGCAAGTGCTGCGAGGACGGCATGCGGGAGAACCCC 2060                2080                2100
       ATGAGGTTCTCGTGCCAGCGCCGGACCCGTTTCATCTCCCTGGGCGAGGCGTGCAAGAAG 2120                2140                2160
       GTCTTCCTGGACTGCTGCAACTACATCACAGAGCTGCGGCGGCAGCACGCGCGGGCCAGC 2180                2200                2220
       CACCTGGGCCTGGCCAGGAGTAACCTGGATGAGGACATCATTGCAGAAGAGAACATCGTT 2240                2260                2280
       TCCCGAAGTGAGTTCCCAGAGAGCTGGCTGTGGAACGTTGAGGACTTGAAAGAGCCACCG 2300                2320                2340
       AAAAATGGAATCTCTACGAAGCTCATGAATATATTTTTGAAAGACTCCATCACCACGTGG 2360                2380                2400
       GAGATTCTGGCTGTCAGCATGTCGGACAAGAAAGGGATCTGTGTGGCAGACCCCTTCGAG 2420                2440                2460
       GTCACAGTAATGCAGGACTTCTTCATCGACCTGCGGCTACCCTACTCTGTTGTTCGAAAC 2480                2500                2520
       GAGCAGGTGGAAATCCGAGCCGTTCTCTACAATTACCGGCAGAACCAAGAGCTCAAGGTG 2540                2560                2580
       AGGGTGGAACTACTCCACAATCCAGCCTTCTGCAGCCTGGCCACCACCAAGAGGCGTCAC 2600                2620                2640
       CAGCAGACCGTAACCATCCCCCCCAAGTCCTCGTTGTCCGTTCCATATGTCATCGTGCCG 2660                2680                2700
       CTAAAGACCGGCCTGCAGGAAGTGGAAGTCAAGGCTGCCGTCTACCATCATTTCATCAGT 2720                2740                2760
       GACGGTGTCAGGAAGTCCCTGAAGGTCGTGCCGGAAGGAATCAGAATGAACAAAACTGTG 2780                2800                2820
       GCTGTTCGCACCCTGGATCCAGAACGCCTGGGCCGTGAAGGAGTGCAGAAAGAGGACATC 2840                2860                2880
       CCACCTGCAGACCTCAGTGACCAAGTCCCGGACACCGAGTCTGAGACCAGAATTCTCCTG 2900                2920                2940
       CAAGGGACCCCAGTGGCCCAGATGACAGAGGATGCCGTCGACGCGGAACGGCTGAAGCAC 2960                2980                3000
```

Figure 2D Continuation of (SEQID2) ProC3 DNA/RNA sequence

```

CTCATTGTGACCCCCTCGGGCTGCGGGGAACAGAACATGATCGGCATGACGCCCACGGTC 3020              3040              3060
ATCGCTGTGCATTACCTGGATGAAACGGAGCAGTGGGAGAAGTTCGGCCTAGAGAAGCGG 3080              3100              3120
CAGGGGGCCTTGGAGCTCATCAAGAAGGGGTACACCCAGCAGCTGGCCTTCAGACAACCC 3140              3160              3180
AGCTCTGCCTTTGCGGCCTTCGTGAAACGGGCACCCAGCACCTGGCTGACCGCCTACGTG 3200              3220              3240
GTCAAGGTCTTCTCTCTGGCTGTCAACCTCATCGCCATCGACTCCCAAGTCCTCTGCGGG 3260              3280              3300
GCTGTTAAATGGCTGATCCTGGAGAAGCAGAAGCCCGACGGGGTCTTCCAGGAGGATGCG 3320              3340              3360
CCCGTGATACACCAAGAAATGATTGGTGGATTACGGAACAACAACGAGAAAGACATGGCC 3380              3400              3420
CTCACGGCCTTTGTTCTCATCTCGCTGCAGGAGGCTAAAGATATTTGCGAGGAGCAGGTC 3440              3460              3480
AACAGCCTGCCAGGCAGCATCACTAAAGCAGGAGACTTCCTTGAAGCCAACTACATGAAC 3500              3520              3540
CTACAGAGATCCTACACTGTGGCCATTGCTGGCTATGCTCTGGCCCAGATGGGCAGGCTG 3560              3580              3600
AAGGGGCCTCTTCTTAACAAATTTCTGACCACAGCCAAAGATAAGAACCGCTGGGAGGAC 3620              3640              3660
CCTGGTAAGCAGCTCTACAACGTGGAGGCCACATCCTATGCCCTCTTGGCCCTACTGCAG 3680              3700              3720
CTAAAAGACTTTGACTTTGTGCCTCCCGTCGTGCGTTGGCTCAATGAACAGAGATACTAC 3740              3760              3780
GGTGGTGGCTATGGCTCTACCCAGGCCACCTTCATGGTGTTCCAAGCCTTGGCTCAATAC 3800              3820              3840
CAAAAGGACGCCCCTGACCACCAGGAACTGAACCTTGATGTGTCCCTCCAACTGCCCAGC 3860              3880              3900
CGCAGCTCCAAGATCACCCACCGTATCCACTGGGAATCTGCCAGCCTCCTGCGATCAGAA 3920              3940              3960
GAGACCAAGGAAAATGAGGGTTTCACAGTCACAGCTGAAGGAAAAGGCCAAGGCACCTTG
```

Figure 2E Continuation of (SEQID2) ProC3 DNA/RNA sequence

```
              3980                4000                4020
TCGGTGGTGACAATGTACCATGCTAAGGCCAAAGATCAACTCACCTGTAATAAATTCGAC 4040                4060                4080
CTCAAGGTCACCATAAAACCAGCACCGGAAACAGAAAAGAGGCCTCAGGATGCCAAGAAC 4100                4120                4140
ACTATGATCCTTGAGATCTGTACCAGGTACCGGGGAGACCAGGATGCCACTATGTCTATA 4160                4180                4200
TTGGACATATCCATGATGACTGGCTTTGCTCCAGACACAGATGACCTGAAGCAGCTGGCC 4220                4240                4260
AATGGTGTTGACAGATACATCTCCAAGTATGAGCTGGACAAAGCCTTCTCCGATAGGAAC 4280                4300                4320
ACCCTCATCATCTACCTGGACAAGGTCTCACACTCTGAGGATGACTGTCTAGCTTTCAAA 4340                4360                4380
GTTCACCAATACTTTAATGTAGAGCTTATCCAGCCTGGAGCAGTCAAGGTCTACGCCTAT 4400                4420                4440
TACAACCTGGAGGAAAGCTGTACCCGGTTCTACCATCCGGAAAAGGAGGATGGAAAGCTG 4460                4480                4500
AACAAGCTCTGCCGTGATGAACTGTGCCGCTGTGCTGAGGAGAATTGCTTCATACAAAAG 4520                4540                4560
TCGGATGACAAGGTCACCCTGGAAGAACGGCTGGACAAGGCCTGTGAGCCAGGAGTGGAC 4580                4600                4620
TATGTGTACAAGACCCGACTGGTCAAGGTTCAGCTGTCCAATGACTTTGACGAGTACATC 4640                4660                4680
ATGGCCATTGAGCAGACCATCAAGTCAGGCTCGGATGAGGTGCAGGTTGGACAGCAGCGC 4700                4720                4740
ACGTTCATCAGCCCCATCAAGTGCAGAGAAGCCCTGAAGCTGGAGGAGAAGAAACACTAC 4760                4780                4800
CTCATGTGGGGTCTCTCCTCCGATTTCTGGGGAGAGAAGCCCAACCTCAGCTACATCATC 4820                4840                4860
GGGAAGGACACTTGGGTGGAGCACTGGCCTGAGGAGGACGAATGCCAAGACGAAGAGAAC 4880                4900                4920
CAGAAACAATGCCAGGACCTCGGCGCCTTCACCGAGAGCATGGTTGTCTTTGGGTGCCCC

AACTGA
```

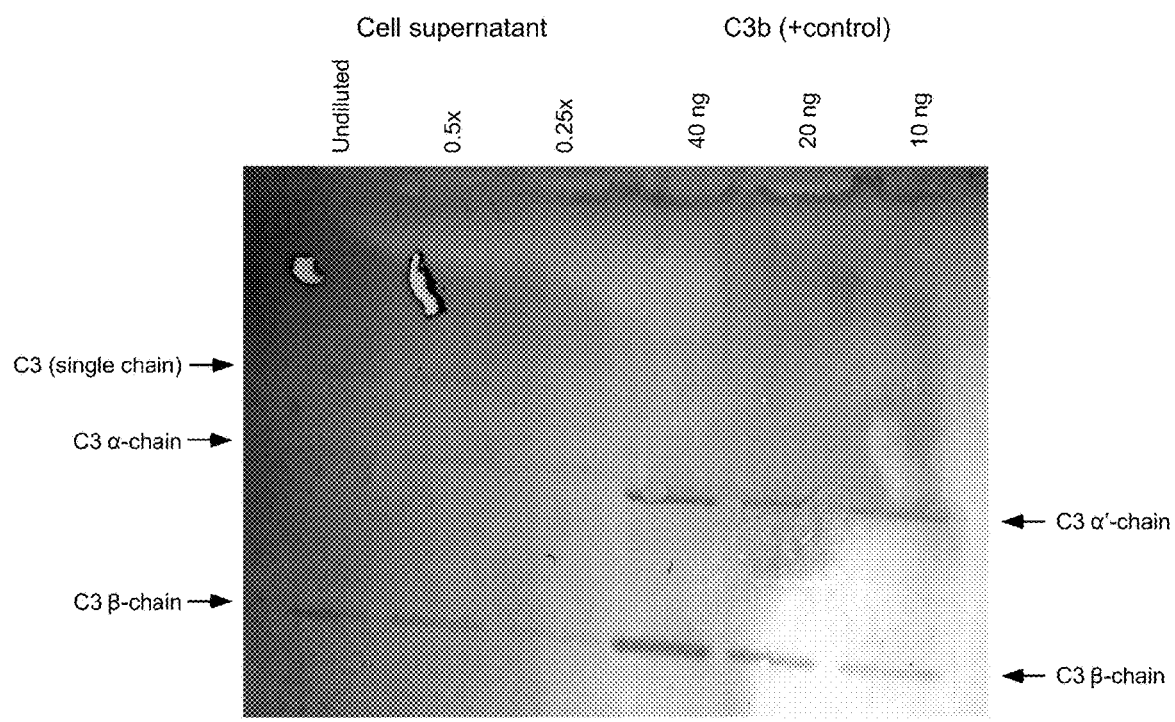
Figure 3 Expression of modified C3 in Baculovirus-infected Sf9 cells.

MODULATORS OF COMPLEMENT FUNCTION

The current application claims a priority to the U.S. Provisional Patent application Ser. No. 62/238,512 filed on Oct. 7, 2015.

FIELD OF THE INVENTION

The invention relates generally to a modified human C3 protein containing a number of single amino acid changes in the α- and β-chain of human C3 protein, designed to increase the affinity of the modified protein to factor B or its active peptide Bb, to decrease the affinity of the modified protein to factor H, and to reduce the immunogenicity of the modified protein as compared to native human C3 protein; a nucleotide sequence encoding the modified C3 protein; a plasmid or viral vector containing the nucleotide sequence for expression the modified C3 protein; and a host cell containing the plasmid or viral vector. The invention also relates to a polyethylene glycol covalently bound to the modified C3 protein for reducing immunogenicity and increasing plasma half-life of the modified C3 protein; a method for depleting complement in a patient by administering the modified C3 protein to the patient in an amount effective to deplete complement; and a method of ameliorating effects caused by certain diseases or a method of ameliorating reperfusion injury in a patient by delivering an effective amount of the modified C3 protein sufficient to deplete complement.

BACKGROUND OF THE INVENTION

The third component of complement, C3, plays an extremely important role in all three of the complement activation pathways, the classical, alternative and lectin pathways (1, 2, 3). In addition, many of the C3 activation products have important functions in immune response and host defense (4, 5). In all the activation pathways, activated C3, called C3b, is a structural subunit of the C3 convertase. The convertase is formed when C3b binds to another complement protein, factor B, which is cleaved by another complement protein, factor D. This yields the activation peptides of factor B, Ba, and Bb, where Bb binds to C3b. This C3 convertase C3b,Bb, is then able to activate more C3 molecules in a similar manner. This cleavage also breaks a high-energy thioester linkage, allowing the covalent attachment of C3b to nearby cell surfaces (6). As more C3 molecules are activated, a tri-molecular complex C3b2,Bb (the C5 convertase), will be formed, which is able to activate C5.

There is a C3 analogue found in cobra venom, called cobra venom factor (CVF) that is a structurally and functionally similar to C3b (7) Like C3b, CVF is able to bind factor B, which is cleaved by factor D to yield a C3/C5 convertase, CVF,Bb. Similar to C3b,Bb, CVF,Bb is able to cleave C3 molecules in an identical manner. However, the CVF-containing convertase is intrinsically far more stable than the C3b,Bb convertase (8). It is also resistant to regulation by a number of complement regulatory proteins. Finally, unlike C3b,Bb, CVF,Bb acts in the fluid phase rather than on cell surfaces, and is able to activate C5 without binding an additional C3b.

CVF and C3 have also been shown to be quite similar structurally. This similarity is reflected in protein sequence similarity, electron microscopic ultrastructure, and most importantly, three-dimensional structure as determined by x-ray crystallography (8, 9). However, there are differences. C3 is a 2-chain molecule with a molecular mass of about 180 kDaltons, while CVF has a 3-chain structure, with a mass of about 149 kDaltons, resembling the C3c, one of the breakdown products of C3b (8, 10).

Because the complement system is involved in a number of different diseases, including some that are wide spread (4, 5), there has been a great deal of research in drugs that inhibit complement activation. CVF, and CVF-like proteins are unique in that they are able to deplete complement through exhaustive complement activation (11). Using a C3-like protein with CVF-like properties and low immunogenicity would be a novel means of stopping complement activation (12).

SUMMARY OF THE INVENTION

The following listing of embodiments is a non-limiting statement of various aspects of the invention. Other aspects and variations will be evident in light of the entire disclosure.

Some embodiments include the replacement of one or more individual amino acids between amino acids 1490 and 1642 (proC3 numbering, FIG. 1, SEQ ID NO:1) of human C3, such that the modified C3 protein forms a more stable complex with factor B and its activated form, Bb. Some embodiments include the replacement of one or more individual amino acids between positions 730 and 1350, such that the modified C3 has less affinity for factor H short consensus repeats (SCR), 1-4 and SCRs 19-20 (13, 14). Some embodiments contain amino acid substitutions between positions 1 and 1642 such that the resulting protein shows less immunogenicity than native C3. Some embodiments will have the amino acid substitutions designed to increase affinity for Bb while decreasing the affinity for factor H. Some embodiments will have amino acid substitutions designed to increase the affinity of the modified C3 protein for Bb while decreasing the immunogenicity of the protein. Some embodiments will have amino acid substitutions designed to decrease affinity for factor H while decreasing the immunogenicity of the modified C3 protein. Some embodiments will have amino acid substitutions designed to increase the affinity of the modified C3 protein for Bb, decrease the affinity for factor H and decrease the immunogenicity of the resulting protein. In some embodiments, the modified protein will cleave C3 but not C5.

In some embodiments, the modified C3 protein can be expressed as a single chain protein. In some embodiments, the modified C3 protein can be cleaved into at least two chains in a form that resembles C3. In further embodiments, the modified C3 protein can be cleaved to release a C3a portion therefrom. The entire C3a sequence (amino acid residues 650 through 726 of SEQ ID NO:1, SVQLTEKRMDKVGKYPKELRKCCEDGMREN-PMRFSCQRRTRFISLGEAC KKVFLDCCNYITELRRQHARASHLGLAR) can be removed, such that the modified protein has the same structure as C3b. In some embodiments, the amino acids involved in the thioester linkage can be changed, such that the thioester linkage is unable to form, wherein C988 is substituted by one of the amino acids: S, T, Q, or N.

In some embodiments, the modified protein can have an additional 1 to 19 amino acids at the N-terminus that are not encoded by C3 nucleic acids. In some embodiments, the modified protein can include a non-C3 signal peptide, such as a *Drosophila* Bip signal sequence. In some embodiments, the modified C3 protein can have modified affinity for factor B and/or factor D. In some embodiments, the modified protein can show partial or complete resistance to Factor H and/or Factor I. In some embodiments, the modified protein can be essentially non-immunogenic.

Other embodiments can include a method for depleting complement by administering a modified C3 protein to a patient in an amount effective for the depletion of complement. In some embodiments, the administration can be local. In further embodiments, the local administration can be into an organ, subcutaneously, into a cavity, or into a tissue. In other embodiments, the local administration can employ a targeting function capable of concentrating the modified C3 protein in a desired location. In further embodiments, the targeting function can include using an antibody conjugated to the modified C3 protein. In some embodiments, the administration can be a systemic administration, such as intravenous or intraperitoneal.

Further embodiments can be methods for avoiding or ameliorating reperfusion injury in a patient by delivering an effective amount of a modified C3 protein to the patient, sufficient to deplete complement; and permitting reperfusion in the patient. Some embodiments can be methods for ameliorating effects caused by the following disease conditions: Neuromyelitis Optica, Multiple Sclerosis, Myasthenia Gravis, Rheumatoid arthritis, wet and dry Age-Related Macular Degeneration, Hemoglobin Urinary Syndrome, Paroxysmal Nocturnal Hemoglobinuria, Inflammatory Bowel Disease, Crohn's Disease, Gout, Alzheimer's disease, Parkinson's Disease, Amyotrophic Lateral Sclerosis, Familial Mediterranean Fever, Dengue Fever, Injury, Dense Deposit Disease, C3 Glomerulonephritis, Neuropathic Pain, Inflammatory Pain, or any disease where inappropriate complement activation contributes to the disease process (5, 8). In some embodiments, the delivering step can include injecting the modified C3 protein into an artery. In other embodiments, the delivering step can include a local delivery of the modified C3 protein. In other embodiments, the delivering step can include a systemic delivery of the modified C3 protein. In some embodiments, reperfusion can be opening a blocked artery. In some embodiments, the reperfusion can occur in connection with transplantation of an organ. In some embodiments, the modified protein could also have polyethylene glycol covalently bound to the n-terminus, the c-terminus, any, some, or all lysines. The bound polyethylene glycol would increase the half-life and stability in the blood following parenteral injection, while decreasing immunogenicity. Polyethylene glycol could also be bound to any, some, or all of the other amino acids of the protein.

Other embodiments include methods of selecting a modified C3 protein, by characterizing at least one property of the modified C3 protein to form a function profile of the modified protein; and matching the function profile with a disease or condition to be treated. In some embodiments, at least one property can be selected from the group consisting of: convertase activity, convertase formation, convertase stability, susceptibility to Factor H, susceptibility to Factor I, ability to cleave C3, and ability to cleave C5. In some embodiments, the selected C3 protein participates in formation of a convertase adapted for treatment of a chronic condition. In some embodiments, the adaptation can be any of the following: longer plasma half-life, greater stability, greater resistance to Factor H, and greater resistance to Factor I. In some embodiments, the convertase can be adapted for treatment of a reperfusion injury. In other embodiments, the adaptation can be any of, high convertase activity, resistance to Factor H, and resistance to Factor I.

Some embodiments include a nucleic acid sequence encoding a modified C3 protein, and/or a vector including the nucleic acid and/or a host cell containing the vector. In some embodiments, the host cell can be any of the following: a *Drosophila* S2 cell, an Sf9 cell, a CHO cell, a COS-7 cell, a High Five™ cell, a yeast cell, a BHK cell, and an HEK293 cell. Some embodiments include a composition that can include the modified human complement C3 protein and a pharmaceutically acceptable carrier and/or the nucleic acid encoding the modified C3 protein. Some embodiments include an expression system expressing the modified C3 protein. In some embodiment, the expression system include a cell selected from the group consisting of: a *Drosophila* S2 cell, an Sf9 cell, a CHO cell, a COS-7 cell, a High Five™ cell, a yeast cell, a BHK cell, and an HEK293 cell.

BRIEF DESCRIPTION OF THE DRAWINGS

FIG. 1A describes the amino acid sequence of human ProC3 (SEQ ID NO:1).

FIG. 1B is a continuation of the amino acid sequence of human ProC3 (SEQ ID NO:1).

FIG. 2A describes the nucleotide sequence of human ProC3 (SEQ ID NO:2).

FIG. 2B is a continuation of the nucleotide sequence of human ProC3 (SEQ ID NO:2).

FIG. 2C is a continuation of the nucleotide sequence of human ProC3 (SEQ ID NO:2).

FIG. 2D is a continuation of the nucleotide sequence of human ProC3 (SEQ ID NO:2).

FIG. 2E is a continuation of the nucleotide sequence of human ProC3 (SEQ ID NO:2).

FIG. 3 shows expression of modified C3 in Baculovirus-infected Sf9 cells. Western blot showing expression of sC3 in the Baculovirus insect expression system. Different amounts of supernatant from HighFive cells infected with recombinant Baculovirus are shown on the left three lanes. As a positive control, purified C3b was run on the three lanes on the right. C3b consists of 2 chains, the α'-chain and the β-chain. There are three bands immune-reacting bands in the expressed protein, the β-chain, the α-chain, and protein that has not been processed (pro-sC3). The α'-chain is the α-chain from which the 77 amino acid C3a has been removed. The presence of the single-chain form of C3 shows that the protease responsible for the maturation of pro-C3 to C3 is only present in the Baculovirus supernatants in very limited amounts.

DETAIL DESCRIPTIONS OF THE INVENTION

Previous studies on human C3/CVF hybrid proteins have shown it is possible to prepare C3 proteins with substitutions of CVF sequences that have many of the properties of CVF, including formation of a stable convertase, reduced factor H affinity, and low immunogenicity (12). Combining these studies with the available crystal structures of C3b, CVF, C3b complexed with factor Bb, CVF in a complex with factor B, C3b bound to factor H (SCRs 1 to 4), and C3b bound to factor H (SCRs 19 and 20) (8, 13, 14) has suggested which individual amino acid substitutions may allow the formation of more stable convertases and which amino acid substitutions may reduce the affinity of C3b for factor H, thereby increasing the stability of modified C3 proteins in vivo. Additionally, computer programs online, such as the Immune Epitope Database from National Institute of Allergy and Infectious Disease (www.iedb.org/ home_v3.php) are able to predict which amino acid sequences within a protein increase the immunogenicity of the protein.

Example 1: Production of Modified Human C3 Proteins

There are numerous amino acid substitutions in human C3 that should produce a modified human C3 that would have a higher affinity for factor B, thus forming a more stable convertase, a lower affinity for factor H, thus increasing the stability of the modified C3 in vivo, and will decrease the immunogenicity of the modified C3 protein.

It has been well documented in the complement literature that Cobra Venom Factor (CVF) forms a more physiochemically stable C3 convertase (CVF,Bb) than does human C3b (6), with a half-life of dissociation of 7 hours at 37° C., versus 1.5 minutes for the C3b-containing convertase. Crystal structures have been derived for CVF,B and C3b,Bb, and interactions between CVF or C3 and factor B (or Bb, respectively) have been determined from the crystal structures. A comparison of the ionic and non-ionic interactions were used to identify the amino acid residues of the C3 protein that interact with factor B or Bb, in which possible amino acid substitutions would result in a more stable C3 convertase. What follows is a list of some of the mutations: P1518N, Q, H, S, T, or β-hydroxy-norvaline; S1550N, D, E, Q, V, I, L, or L-Glu-γ-hydrazide; V1637N, T, S, E, Q, D, or mono-4-fluoroglutamic Acid; N1642I, E, D, Q, T, S, or β-hydroxy-norvaline; G1519I, T, S, V, L, A, N, Q, H, D, E, or L-Glu-γ-hydrazide; A1543Q, S, T, V, L, D, E, N, I, or L-threo-β-hydroxyl-aspartic acid; I1544G, K, W, V, 3-fluoro-valine, L-t-butyl-glycine, L-threonine, or L-allo-threonine; E1545D, N, Q, S, T, 5,5',5'-trifluoro-leucine, or β-t-butyl-alanine; Q1546S, T, M, A, D, E, N, mono-4-fluoro-glutamic acid, or 4,4-difluoro-glutamic acid; T1547A, V, L, I, G, W, 3-fluoro-valine, L-t-butyl-glycine; V1555T, S, D, N, Q, E, or L-Glu-γ-hydrazide; Q1556L, I, M, V, G, P, thiazolidine-2-carboxylic acid, thiazolidine-4-carboxylic acid, 3,4-dehydro-proline, or L-azetidine-2-carboxylic acid; V1557S, T, N, Q, D, E, R, H, K, or L-canavanine; Q1559L, R, H, K, N, Q, S-2-aminoethylcysteine, or dehydrolysine; E1633L, M, I, Y, W, F, 3-fluoro-L-tyrosine, or 3-nitro-L-tyrosine; V1636T, S, D, E, or β-hydroxynorvaline; A1630Q, N, T, S, D, E, or L-Glu-γ-hydrazide.

The crystal structures of factor H (CCPs 1-4 or CCPs 19-20) complexed with C3b have been derived (13, 14). The structures were used to map the ionic and non-ionic interactions between the two proteins. These interactions suggested amino acid substitutions on C3b that may reduce the strength of the interactions between the two proteins, either with substitutions that will eliminate ionic interactions, or that change the character of amino acids involved in non-ionic interactions between the two proteins by replacing polar residues with non-polar residues, or by making substitutions where a bulky residue is replaced by a small one (e.g. a tryptophane with an alanine or glycine). What follows is a list of the mutations: D733G, A, or V; I734F, W, or Y; E738S, or T; N739D, E, L, I, or V; H897D, E, T, S, G, A, V, L, or I; H898A, G, V, D, E, I, or L; K1030T, S, D, E, M, L, or I; T1033G, A, V, L, or I; V1049T, N, Q, D, or E; Q1140W, Y, F, M, S, T, D, or E; T1287R, K, H, N, or Q; H1291F, W, Y, I, L, S, T, D, or E; K1285P, V, A, G, F, D, or E; L1298G, A, or V.

Potentially immunogenic regions of human C3 were determined using available internet programs, and substitutions designed by using similar amino acid residues that are less immunogenic but similar enough to the original residue to prevent loss of function. E176D, S, T, or L; V178A, I, L, M, or G; Q182N, S, T, I, or V; W183F, Y, M, or L; K184H, R, or Y; Y1173F, M, L, or I; A1174G, or V; Q1177N, S, or T; M1178L, I, or V; R1180H, K, T, S, Q, or N; K1182H, R, N, Q, T, or S; K1194R, Q, or N; N1197Q, S, or T; W1199F, Y, M, L, or I; K1204R, H, N, or Q; Y1207L, I, M, or V; V1232A, or G; R1233H, K, N, or Q; W1234F, Y, M, or L; E1237D; Q1238N, T, or S; R1239H, K, N, or Q; Y1240F, M, L, or I; W781F, Y, M, L, or V; I783L, M, V, or A; L784I, M, or V; M788L, I, V, or A; K791A, L, N, or Q; Y5F, W, L, I, or M; I7L, V, or A; S17T, N, or D; R14H, K, N, or Q; E1210N, S, or T; Y1214F, W, I, L, M, or V; L1216I, M, or A; Q1221N, T, or S; K1223R, H, N, or Q; F1252Y, W, L, I, or V; M1253L, I, or V; F1255Y, W, L, I, or V; Q1256N, or T; Y1261W, F, M, I, or L; K115H, R, Q, or N; I117L, V, or A; Y118F, W, L, M, or I; Y513F, W, L, M, or I; Y514F, W, L, M, or I; L516I, V, or A; I517L, V, or A; S520T, D, or E.

Stabilization of the protein could also be increased by the attachment of polyethylene glycol on the modified C3 protein.

Since the preparation of many/most of the modified C3 proteins will involve producing coding sequences with several amino acid substitutions based on the nucleotide sequence (FIG. 2, SEQ ID NO:2) encoding the native human C3 protein (FIG. 1, SEQ ID NO:1), the most efficient method to produce these proteins would involve using synthesizing the entire coding sequence of the modified protein with the desired amino acid substitutions and the desired restriction enzyme recognition sequences at the 5' and 3' ends of the coding sequence.

Example 2: Expression of Modified Human C3 Proteins

Modified C3 proteins will be expressed in either *Drosophila* S2 cells, in Baculovirus-infected Sf9 (FIG. 3) or HighFive™ cells, or, for final production in a mammalian protein expression system, such as in COS7 or CHO cells. For production in *Drosophila* S2 cells, the *Drosophila* BiP signal sequence will be used so that the expressed proteins will be exported to the media. Plasmids containing DNA coding for the modified C3 proteins described above will be cloned into one of the *Drosophila* S2 expression plasmids (pMT/BiP-V5-HisA, . . . HisB, or . . . HisC). Use of these plasmids allows expression of the proteins with the *Drosophila* BiP signal sequence, thus ensuring high expression and export in S2 cells. pMT/BiP-V5-HisA, B, or C plasmids containing the coding sequence of a modified C3 protein will be transfected into *Drosophila* S2 cells using the calcium phosphate method of Chen and Okayama (15). S2 cells were transfected with a mixture of expression plasmid and pCoBlast, using a ratio of 19:1 (w:w). Following transfection, cells containing both plasmids were selected using blasticidin (25 μg/ml). For expression, 1-liter cultures of transfected cells were grown in serum-free medium (High Five™ plus L-glutamine), in the absence of blasticidin. When the cells reached a density of $5 \times 10^6$ cells/ml, production of the recombinant proteins was induced by the addition of $CuSO_4$ to a final concentration of 25 μM. Cultures were allowed to express recombinant proteins for 4-5 days. Hybrid proteins were then purified from the media by a combination of ANX, Sephacryl H-300, and CM-FF chromatography.

For Baculovirus-infected insect cell production of modified C3 proteins, the coding sequences will be cloned into the Baculovirus co-transfection plasmid pBacPAK8. The C3-coding sequence containing plasmid will then be co-transfected into insect cells (Sf9 or HighFive™), using a lipotransfection reagent (16). The cells will be allowed to grow for 4-5 days at 27° C. The cell supernatant will be centrifuged to remove cell debris, and approximately 0.5 ml of the P0 virus stock will be used to infect Sf9 or HighFive™ cells growing in log phase. Cells will be removed by centrifugation. This is the P1 virus stock. This stock will be used to infect Sf9 cells at an MOI of 0.1, to create the P2 virus stock, which needs to be filtered through 0.2 micron filters to ensure the removal of all cellular debris. This is repeated to prepare the P3 virus stock, which should have a titer of >5×10$^8$ pfu/ml. This stock is used for protein expression.

For protein expression in Baculovirus-infected cells, cultures in growing in log phase will be infected the P3 supernatant at an MOI of 3. The culture will be harvested at a time that had been previously determined, and the cells separated from the supernatant by centrifugation.

For expression of modified C3 proteins in mammalian cells, coding sequences for modified C3 proteins will be cloned into pSecTag2A, B, or C, depending on the restriction sites at either end of the modified C3 coding sequence. Since these vectors contain the mouse IgK secretion signal, the coding sequence insert will not contain the human C3 signal sequence (17). Coding sequences will be cut with the appropriate restriction enzymes, and ligated into the appropriate pSecTag2/Hygro vector cut with the same enzymes. Following ligation, plasmids will be transformed into *E. coli* DH5αF', and plated out on LB plates containing 100 µg/ml Ampicillin. Plasmids will be isolated, and correct clones determined by restriction mapping and sequencing. Plasmids will be transfected into COST cells using the Lipofectamine transfection protocol. Cells containing the Hygromycin B resistance gene will be selected by culturing the cells in media containing varying concentrations of Hygromycin B. Expression of the modified C3 will be determined by PAGE on cell supernatants, and detection using goat anti-human C3 antibodies.

Example 3: Activity Measurements of Modified Human C3 Proteins

The purified modified human C3 proteins will be subjected to a number of functional analyses as follows.
Complement Depletion This assay measures the ability of a protein to deplete complement in human (or other) serum. The assay was done in two steps. In the first step, the protein of interest will be diluted to the desired concentrations in buffer, usually by serial dilution (typically from less than a nanogram/microliter up to approximately 320 ng/microliter or 3.2 µg in the 10 microliters used in the assay). Then, a 1 µL aliquot of the diluted protein will be mixed with 9 µL undiluted serum. The mixture will be incubated at 37° C. for 3 hours, allowing the protein to exhaustively activate and thus deplete C3 and factor B in the serum. Then, to measure the amount of complement activity left, the serum will be diluted and mixed with antibody-sensitized sheep erythrocytes, which are easily lysed by complement when it is present in serum. This reaction will be allowed to proceed for 30 minutes, and will be stopped by diluting the mixture in cold buffer. The cells will be centrifuged and the lysed cells quantified by measuring the hemoglobin released (12).
Factor B Activation Assay This is an assay to measure the ability of a modified protein to activate factor B and form a C3/C5 convertase. The convertase formation will be measured as a function of the cleavage of factor B into Bb and Ba. In the assay, purified modified C3 proteins will be incubated with a three-fold molar excess of factor B and catalytic amounts of factor D (all highly purified) in the presence of magnesium at 37° C. At various times, aliquots of the reaction will be withdrawn, and the reaction stopped by adding EDTA, which chelates the magnesium. The reaction products will be run on a non-reducing SDS-polyacrylamide gel, which will be stained for proteins with Coomassie Blue. The amount of Factor B converted will be quantified by scanning the gel into a specialized computer program and measuring the amount of protein in the factor B and Bb bands. The results of this assay are dependent on both the rate of factor B activation and the stability of the resulting convertase. Since there is an excess of factor B in the reaction, a very rapid production of Ba and Bb would indicate an unstable convertase (12).
C3 Convertase Activity Assay This assay measures the activity of C3/C5 convertases containing modified proteins to activate human C3, by cleaving off the C3a peptide. To perform this assay, convertases will be formed as described above, and the reaction stopped by the addition of EDTA. The convertase will then be mixed with human C3, and the reaction incubated at 37° C. At the indicated times, aliquots will be removed, and the reaction stopped by mixing with gel loading buffer containing SDS and β-mercaptoethanol. The SDS denatures the proteins, and the β-mercaptoethanol reduces the disulfide bonds between cysteines in the proteins. After electrophoresis under reducing conditions, the gel will be stained with Coomassie Blue dye, and the relative amounts of the C3a-chain and the C3a-chain will be quantified as described above. Care is taken to use the same amount of convertase in each reaction. The results of this assay are dependent both on the activity of the modified C3-containing convertase and its stability, as an active but unstable convertase will rapidly cleave C3, but will stop as the convertase dissociates (12).
Assay for Cleavage of Modified C3 Proteins by Factors H and I Modified C3 proteins will incubated with purified human Factor H and Factor I at 37° C. for several hours. The reactions are analyzed by subsequent 7% (w/v) SDS polyacrylamide gel electrophoresis under reducing conditions. Factor H binding and I activity is determined by the reduction in the strength of the 105 kDa α'-chain band, and appearance of bands with a molecular weight of 37 and 40 kDa (12).
Assays for Immunogenicity.

Various methods can be used to analyze immunogenicity, including but not limited to, skin tests, testing the modified C3 protein in transgenic animals which have been genetically engineered to have human immune systems, in vitro methods, including RIA tests using serum generated in such transgenic animals, radioimmunoprecipitation assays, ELISA assays, electrochemiluminescence, and Surface Plasmon Resonance. In addition, mouse, rat or guinea pig analogs of some proteins can be constructed, using either mouse, rat or guinea pig C3 sequences. These can be injected into the appropriate animal, and serum is collected and analyzed for the production of antibodies against the modified proteins.

This method measures the stability of the modified C3 protein in plasma in different ways. However, it is to be understood that one or all of the methods can be used as well as any other methods known to one of skill in the art.

The first method measures the stability in serum in vitro. Rabbit serum is isolated and separated from whole blood. Aliquots of different concentrations of the modified C3 proteins that have been biotinylated are added to the serum and allowed to incubate. Aliquots of the serum are removed at various time intervals, and the amount of modified C3 that persists is identified in an ELISA assay using a monoclonal antibody which is specific to human C3. This is one example of animal serum that can be used. The choice of serum will depend on the cross-reactivity of the human C3 antibodies with C3 of that species.

A second method allows the determination of modified C3 in any animal. Modified C3 proteins are biotinylated, and injected into an animal. At times, blood is withdrawn from the animal, and serum separated from the blood. The amount of biotinylated protein can be measured by ELISA, using biotin antibodies (or streptavidin), and the activity of the modified protein measured by measuring the amount of C3 remaining in the serum, using the second part of the complement depletion assay to determine remaining complement activity.

All illustrations of the drawings are for the purpose of describing selected versions of the present invention and are not intended to limit the scope of the present invention.

Although the invention has been explained in relation to its preferred embodiment, it is to be understood that many other possible modifications and variations can be made without departing from the spirit and scope of the invention as hereinafter claimed.

What is claimed is:

1. A human C3 protein (SEQ ID NO:1) or an active fragment thereof (SEQ ID NO:1 without amino acid residues 650 through 726) modified to form a stable C3 convertase, with one or more amino acid replacements selected from the group consisting of: P1518S; S1550N; V1637D; N1642 S; and V1636S, wherein the position of the amino acid residue is based on the sequence of SEQ ID NO:1 numbering.

2. A human C3 protein (SEQ ID NO:1) or an active fragment thereof (SEQ ID NO:1 without amino acid residues 650 through 726) modified such that its affinity for complement factor H is lessened, thus increasing its half-life in vivo, wherein the modified C3 protein consists of one or more amino acid substitutions selected from the group consisting of: D733G; I734F; E738S; N739D; H897E; H898A; K1030T; T1033A; V1049T; Q1140Y; T1287R; H1291I; K1285P; and L1298G, wherein the position of the amino acid residue is based on the sequence of SEQ ID NO:1 numbering.

3. The modified C3 protein according to claim 1 with further sequence changes to decrease its affinity for complement factor H, wherein the sequence changes consist of one or more amino acid substitutions selected from the group consisting of: D733G; I734F; E738S; N739D; H897E; H898A; K1030T; T1033 A; V1049T; Q1140Y; T1287R; H1291I; K1285P; and L1298G.

4. The modified C3 protein according to claim 1 with polyethylene glycol covalently bound to the N-terminus, C-terminus, or a lysine residue on the modified protein, wherein the bound polyethylene glycol increases the half-life and stability of the modified protein in the blood when the modified C3 protein is injected parenterally, and reduces the immunogenicity of the modified protein, and wherein prior to the polyethylene glycol binding reaction, the active site of the modified protein is protected from alteration by pre-incubating with staphylococcal complement inhibitor protein (SCIN).

5. The modified C3 protein according to claim 1 with further sequence changes by adding 1 to 19 amino acids of a non-C3 signal peptide to the N-terminus of the modified protein.

6. The modified C3 protein according to claim 5, wherein the non-C3 signal peptide is a *Drosophila* BiP sequence or a mammalian signal peptide.

7. A composition comprising the modified C3 protein according to claim 1 or 2 and a pharmaceutically acceptable carrier.

8. A method for depleting complement in a patient by administering the modified C3 protein according to claim 1 to the patient in an amount effective to deplete complement.

9. The method according to claim 8, wherein the modified C3 protein is locally administered into an organ or subcutaneously administered into a cavity or a tissue.

10. The method according to claim 8, wherein the administration is a systemic administration, and the systemic administration is intravenous or intraperitoneal.

11. A method for avoiding or ameliorating reperfusion injury in a patient by delivering an effective amount of the modified C3 protein according to claim 1, sufficient to deplete complement and permit reperfusion in the patient.

12. The method according to claim 11, wherein the delivery step is a step of injecting the modified C3 protein into an artery, a local delivery or a systemic delivery.

13. The method according to claim 11, wherein the reperfusion is opening a blocked artery, or the reperfusion occurs in connection with transplantation of an organ.

14. The method according to claim 11, wherein the modified C3 protein has polyethylene glycol covalently bound to the N-terminus, C-terminus or a lysine residue of the modified protein, and wherein the bound polyethylene glycol increases the half-life and stability of the modified C3 protein in the blood after parenteral injection and decreases immunogenicity.

15. A method for ameliorating effects caused by a disease comprising delivering an amount of the modified C3 protein according to claim 1 effective to deplete complement, wherein the disease is selected from the group consisting of: Neuromyelitis Optica, Multiple Sclerosis, Myasthenia Gravis, Rheumatoid arthritis, wet and dry Age-Related Macular Degeneration, Hemoglobin Urinary Syndrome, Paroxysmal Nocturnal Hemoglobinemia, Inflammatory Bowel Disease, Crohn's Disease, Alzheimer's disease, Parkinson's Disease, Amyotrophic Lateral Sclerosis, Familial Mediterranean Fever, Dengue Fever, Cardiac or any Reperfusion Injury, Gout, Dense Deposit Disease, C3 Glomerulonephritis, Neuropathic Pain, and Inflammatory Pain.

16. A composition comprising the modified C3 protein according to claim 3 and a pharmaceutically acceptable carrier.

* * * * *

SEQUENCE LISTING

<160> NUMBER OF SEQ ID NOS: 2

<210> SEQ ID NO 1
<211> LENGTH: 1642
<212> TYPE: PRT
<213> ORGANISM: Homo sapiens

<400> SEQUENCE: 1

Gly Ser Pro Met Tyr Ser Ile Ile Thr Pro Asn Ile Leu Arg Leu Glu
 1               5                  10                  15

Ser Glu Glu Thr Met Val Leu Glu Ala His Asp Ala Gln Gly Asp Val
            20                  25                  30

Pro Val Thr Val Thr Val His Asp Phe Pro Gly Lys Lys Leu Val Leu
        35                  40                  45

Ser Ser Glu Lys Thr Val Leu Thr Pro Ala Thr Asn His Met Gly Asn
    50                  55                  60

Val Thr Phe Thr Ile Pro Ala Asn Arg Glu Phe Lys Ser Glu Lys Gly
65                  70                  75                  80

Arg Asn Lys Phe Val Thr Val Gln Ala Thr Phe Gly Thr Gln Val Val
                85                  90                  95

Glu Lys Val Val Leu Val Ser Leu Gln Ser Gly Tyr Leu Phe Ile Gln
            100                 105                 110

Thr Asp Lys Thr Ile Tyr Thr Pro Gly Ser Thr Val Leu Tyr Arg Ile
        115                 120                 125

Phe Thr Val Asn His Lys Leu Leu Pro Val Gly Arg Thr Val Met Val
    130                 135                 140

Asn Ile Glu Asn Pro Glu Gly Ile Pro Val Lys Gln Asp Ser Leu Ser
145                 150                 155                 160

Ser Gln Asn Gln Leu Gly Val Leu Pro Leu Ser Trp Asp Ile Pro Glu
                165                 170                 175

Leu Val Asn Met Gly Gln Trp Lys Ile Arg Ala Tyr Tyr Glu Asn Ser
            180                 185                 190

Pro Gln Gln Val Phe Ser Thr Glu Phe Glu Val Lys Glu Tyr Val Leu
        195                 200                 205

Pro Ser Phe Glu Val Ile Val Glu Pro Thr Glu Lys Phe Tyr Tyr Ile
    210                 215                 220

Tyr Asn Glu Lys Gly Leu Glu Val Thr Ile Thr Ala Arg Phe Leu Tyr
225                 230                 235                 240

Gly Lys Lys Val Glu Gly Thr Ala Phe Val Ile Phe Gly Ile Gln Asp
                245                 250                 255

Gly Glu Gln Arg Ile Ser Leu Pro Glu Ser Leu Lys Arg Ile Pro Ile
            260                 265                 270

```
Glu Asp Gly Ser Gly Glu Val Leu Ser Arg Lys Val Leu Asp
        275                 280                 285
Gly Val Gln Asn Leu Arg Ala Glu Asp Leu Val Gly Lys Ser Leu Tyr
290                 295                 300
Val Ser Ala Thr Val Ile Leu His Ser Gly Ser Asp Met Val Gln Ala
305                 310                 315                 320
Glu Arg Ser Gly Ile Pro Ile Val Thr Ser Pro Tyr Gln Ile His Phe
                325                 330                 335
Thr Lys Thr Pro Lys Tyr Phe Lys Pro Gly Met Pro Phe Asp Leu Met
                340                 345                 350
Val Phe Val Thr Asn Pro Asp Gly Ser Pro Ala Tyr Arg Val Pro Val
                355                 360                 365
Ala Val Gln Gly Glu Asp Thr Val Gln Ser Leu Thr Gln Gly Asp Gly
370                 375                 380
Val Ala Lys Leu Ser Ile Asn Thr His Pro Ser Gln Lys Pro Leu Ser
385                 390                 395                 400
Ile Thr Val Arg Thr Lys Lys Gln Glu Leu Ser Glu Ala Glu Gln Ala
                405                 410                 415
Thr Arg Thr Met Gln Ala Leu Pro Tyr Ser Thr Val Gly Asn Ser Asn
                420                 425                 430
Asn Tyr Leu His Leu Ser Val Leu Arg Thr Glu Leu Arg Pro Gly Glu
                435                 440                 445
Thr Leu Asn Val Asn Phe Leu Leu Arg Met Asp Arg Ala His Glu Ala
                450                 455                 460
Lys Ile Arg Tyr Tyr Thr Tyr Leu Ile Met Asn Lys Gly Arg Leu Leu
465                 470                 475                 480
Lys Ala Gly Arg Gln Val Arg Glu Pro Gly Gln Asp Leu Val Val Leu
                485                 490                 495
Pro Leu Ser Ile Thr Thr Asp Phe Ile Pro Ser Phe Arg Leu Val Ala
                500                 505                 510
Tyr Tyr Thr Leu Ile Gly Ala Ser Gly Gln Arg Glu Val Val Ala Asp
                515                 520                 525
Ser Val Trp Val Asp Val Lys Asp Ser Cys Val Gly Ser Leu Val Val
530                 535                 540
Lys Ser Gly Gln Ser Glu Asp Arg Gln Pro Val Pro Gly Gln Gln Met
545                 550                 555                 560
Thr Leu Lys Ile Glu Gly Asp His Gly Ala Arg Val Val Leu Val Ala
                565                 570                 575
Val Asp Lys Gly Val Phe Val Leu Asn Lys Lys Asn Lys Leu Thr Gln
                580                 585                 590
Ser Lys Ile Trp Asp Val Val Glu Lys Ala Asp Ile Gly Cys Thr Pro
                595                 600                 605
Gly Ser Gly Lys Asp Tyr Ala Gly Val Phe Ser Asp Ala Gly Leu Thr
610                 615                 620
Phe Thr Ser Ser Ser Gly Gln Gln Thr Ala Gln Arg Ala Glu Leu Gln
625                 630                 635                 640
Cys Pro Gln Pro Ala Ala Arg Arg Arg Arg Ser Val Gln Leu Thr Glu
                645                 650                 655
Lys Arg Met Asp Lys Val Gly Lys Tyr Pro Lys Glu Leu Arg Lys Cys
                660                 665                 670
Cys Glu Asp Gly Met Arg Glu Asn Pro Met Arg Phe Ser Cys Gln Arg
                675                 680                 685
```

-continued

```
Arg Thr Arg Phe Ile Ser Leu Gly Glu Ala Cys Lys Lys Val Phe Leu
    690             695             700

Asp Cys Cys Asn Tyr Ile Thr Glu Leu Arg Arg Gln His Ala Arg Ala
705             710             715             720

Ser His Leu Gly Leu Ala Arg Ser Asn Leu Asp Glu Asp Ile Ile Ala
                725             730             735

Glu Glu Asn Ile Val Ser Arg Ser Glu Phe Pro Glu Ser Trp Leu Trp
            740             745             750

Asn Val Glu Asp Leu Lys Glu Pro Lys Asn Gly Ile Ser Thr Lys
                755             760             765

Leu Met Asn Ile Phe Leu Lys Asp Ser Ile Thr Thr Trp Glu Ile Leu
770             775             780

Ala Val Ser Met Ser Asp Lys Lys Gly Ile Cys Val Ala Asp Pro Phe
785             790             795             800

Glu Val Thr Val Met Gln Asp Phe Phe Ile Asp Leu Arg Leu Pro Tyr
                805             810             815

Ser Val Val Arg Asn Glu Gln Val Glu Ile Arg Ala Val Leu Tyr Asn
            820             825             830

Tyr Arg Gln Asn Gln Glu Leu Lys Val Arg Val Glu Leu Leu His Asn
        835             840             845

Pro Ala Phe Cys Ser Leu Ala Thr Thr Lys Arg Arg His Gln Gln Thr
    850             855             860

Val Thr Ile Pro Pro Lys Ser Ser Leu Ser Val Pro Tyr Val Ile Val
865             870             875             880

Pro Leu Lys Thr Gly Leu Gln Glu Val Glu Val Lys Ala Ala Val Tyr
                885             890             895

His His Phe Ile Ser Asp Gly Val Arg Lys Ser Leu Lys Val Val Pro
            900             905             910

Glu Gly Ile Arg Met Asn Lys Thr Val Ala Val Arg Thr Leu Asp Pro
        915             920             925

Glu Arg Leu Gly Arg Glu Gly Val Gln Lys Glu Asp Ile Pro Pro Ala
    930             935             940

Asp Leu Ser Asp Gln Val Pro Asp Thr Glu Ser Glu Thr Arg Ile Leu
945             950             955             960

Leu Gln Gly Thr Pro Val Ala Gln Met Thr Glu Asp Ala Val Asp Ala
                965             970             975

Glu Arg Leu Lys His Leu Ile Val Thr Pro Ser Gly Cys Gly Glu Gln
            980             985             990

Asn Met Ile Gly Met Thr Pro Thr Val Ile Ala Val His Tyr Leu Asp
        995             1000            1005

Glu Thr Glu Gln Trp Glu Lys Phe Gly Leu Glu Lys Arg Gln Gly
    1010            1015            1020

Ala Leu Glu Leu Ile Lys Lys Gly Tyr Thr Gln Gln Leu Ala Phe
    1025            1030            1035

Arg Gln Pro Ser Ser Ala Phe Ala Ala Phe Val Lys Arg Ala Pro
    1040            1045            1050

Ser Thr Trp Leu Thr Ala Tyr Val Val Lys Val Phe Ser Leu Ala
    1055            1060            1065

Val Asn Leu Ile Ala Ile Asp Ser Gln Val Leu Cys Gly Ala Val
    1070            1075            1080

Lys Trp Leu Ile Leu Glu Lys Gln Lys Pro Asp Gly Val Phe Gln
    1085            1090            1095

Glu Asp Ala Pro Val Ile His Gln Glu Met Ile Gly Gly Leu Arg
```

```
            1100                1105               1110
Asn Asn Asn Glu Lys Asp Met Ala Leu Thr Ala Phe Val Leu Ile
        1115            1120               1125
Ser Leu Gln Glu Ala Lys Asp Ile Cys Glu Glu Gln Val Asn Ser
        1130            1135               1140
Leu Pro Gly Ser Ile Thr Lys Ala Gly Asp Phe Leu Glu Ala Asn
        1145            1150               1155
Tyr Met Asn Leu Gln Arg Ser Tyr Thr Val Ala Ile Ala Gly Tyr
        1160            1165               1170
Ala Leu Ala Gln Met Gly Arg Leu Lys Gly Pro Leu Leu Asn Lys
        1175            1180               1185
Phe Leu Thr Thr Ala Lys Asp Lys Asn Arg Trp Glu Asp Pro Gly
        1190            1195               1200
Lys Gln Leu Tyr Asn Val Glu Ala Thr Ser Tyr Ala Leu Leu Ala
        1205            1210               1215
Leu Leu Gln Leu Lys Asp Phe Asp Phe Val Pro Pro Val Val Arg
        1220            1225               1230
Trp Leu Asn Glu Gln Arg Tyr Tyr Gly Gly Gly Tyr Gly Ser Thr
        1235            1240               1245
Gln Ala Thr Phe Met Val Phe Gln Ala Leu Ala Gln Tyr Gln Lys
        1250            1255               1260
Asp Ala Pro Asp His Gln Glu Leu Asn Leu Asp Val Ser Leu Gln
        1265            1270               1275
Leu Pro Ser Arg Ser Ser Lys Ile Thr His Arg Ile His Trp Glu
        1280            1285               1290
Ser Ala Ser Leu Leu Arg Ser Glu Glu Thr Lys Glu Asn Glu Gly
        1295            1300               1305
Phe Thr Val Thr Ala Glu Gly Lys Gly Gln Gly Thr Leu Ser Val
        1310            1315               1320
Val Thr Met Tyr His Ala Lys Ala Lys Asp Gln Leu Thr Cys Asn
        1325            1330               1335
Lys Phe Asp Leu Lys Val Thr Ile Lys Pro Ala Pro Glu Thr Glu
        1340            1345               1350
Lys Arg Pro Gln Asp Ala Lys Asn Thr Met Ile Leu Glu Ile Cys
        1355            1360               1365
Thr Arg Tyr Arg Gly Asp Gln Asp Ala Thr Met Ser Ile Leu Asp
        1370            1375               1380
Ile Ser Met Met Thr Gly Phe Ala Pro Asp Thr Asp Asp Leu Lys
        1385            1390               1395
Gln Leu Ala Asn Gly Val Asp Arg Tyr Ile Ser Lys Tyr Glu Leu
        1400            1405               1410
Asp Lys Ala Phe Ser Asp Arg Asn Thr Leu Ile Ile Tyr Leu Asp
        1415            1420               1425
Lys Val Ser His Ser Glu Asp Asp Cys Leu Ala Phe Lys Val His
        1430            1435               1440
Gln Tyr Phe Asn Val Glu Leu Ile Gln Pro Gly Ala Val Lys Val
        1445            1450               1455
Tyr Ala Tyr Tyr Asn Leu Glu Glu Ser Cys Thr Arg Phe Tyr His
        1460            1465               1470
Pro Glu Lys Glu Asp Gly Lys Leu Asn Lys Leu Cys Arg Asp Glu
        1475            1480               1485
Leu Cys Arg Cys Ala Glu Glu Asn Cys Phe Ile Gln Lys Ser Asp
        1490            1495               1500
```

| | | | | | | | | | | | |
|---|---|---|---|---|---|---|---|---|---|---|---|
| Asp | Lys | Val | Thr | Leu | Glu | Glu | Arg | Leu | Asp | Lys | Ala | Cys | Glu | Pro |
| | 1505 | | | | 1510 | | | | 1515 | | |

Gly Val Asp Tyr Val Tyr Lys Thr Arg Leu Val Lys Val Gln Leu
    1520            1525            1530

Ser Asn Asp Phe Asp Glu Tyr Ile Met Ala Ile Glu Gln Thr Ile
    1535            1540            1545

Lys Ser Gly Ser Asp Glu Val Gln Val Gly Gln Gln Arg Thr Phe
    1550            1555            1560

Ile Ser Pro Ile Lys Cys Arg Glu Ala Leu Lys Leu Glu Glu Lys
    1565            1570            1575

Lys His Tyr Leu Met Trp Gly Leu Ser Ser Asp Phe Trp Gly Glu
    1580            1585            1590

Lys Pro Asn Leu Ser Tyr Ile Ile Gly Lys Asp Thr Trp Val Glu
    1595            1600            1605

His Trp Pro Glu Glu Asp Glu Cys Gln Asp Glu Asn Gln Lys
    1610            1615            1620

Gln Cys Gln Asp Leu Gly Ala Phe Thr Glu Ser Met Val Val Phe
    1625            1630            1635

Gly Cys Pro Asn
    1640

<210> SEQ ID NO 2
<211> LENGTH: 4926
<212> TYPE: DNA
<213> ORGANISM: Homo sapiens

<400> SEQUENCE: 2

```
agtcccatgt actctatcat caccccccaac atcttgcggc tggagagcga ggagaccatg    60
gtgctggagg cccacgacgc gcaaggggat gttccagtca ctgttactgt ccacgacttc   120
ccaggcaaaa aactagtgct gtccagtgag aagactgtgc tgaccccctgc caccaaccac   180
atgggcaacg tcaccttcac gatcccagcc aacagggagt tcaagtcaga aaaggggcgc   240
aacaagttcg tgaccgtgca ggccaccttc gggacccaag tggtggagaa ggtggtgctg   300
gtcagcctgc agagcgggta cctcttcatc agacagaca agaccatcta caccctggc   360
tccacagttc tctatcggat cttcaccgtc aaccacaagc tgctacccgt gggccggacg   420
gtcatggtca acattgagaa cccggaaggc atcccggtca gcaggactc cttgtcttct   480
cagaaccagc ttggcgtctt gcccttgtct tgggacattc cggaactcgt caacatgggc   540
cagtggaaga tccgagccta ctatgaaaac tcaccacagc aggtcttctc cactgagttt   600
gaggtgaagg agtacgtgct gcccagtttc gaggtcatag tggagcctac agagaaattc   660
tactacatct ataacgagaa gggcctggag gtcaccatca ccgccaggtt cctctacggg   720
aagaaagtgg agggaactgc ctttgtcatc ttcgggatcc aggatggcga acagaggatt   780
tccctgcctg aatccctcaa gcgcattccg attgaggatg ctcgggggga ggttgtgctg   840
agccggaagg tactgctgga cggggtgcag aacctccgag cagaagacct ggtggggaag   900
tctttgtacg tgtctgccac cgtcatcttg cactcaggca gtgacatggt gcaggcagag   960
cgcagcggga tccccatcgt gacctctccc taccagatcc acttcaccaa gacacccaag  1020
tacttcaaac aggaatgcc ctttgacctc atggtgttcg tgacgaaccc tgatggctct  1080
ccagcctacc gagtccccgt ggcagtccag ggcgaggaca ctgtgcagtc tctaacccag  1140
ggagatggcg tggccaaact cagcatcaac acacaccccca gccagaagcc cttgagcatc  1200
```

-continued

```
acggtgcgca cgaagaagca ggagctctcg gaggcagagc aggctaccag gaccatgcag    1260
gctctgccct acagcaccgt gggcaactcc aacaattacc tgcatctctc agtgctacgt    1320
acagagctca gacccgggga gaccctcaac gtcaacttcc tcctgcgaat ggaccgcgcc    1380
cacgaggcca agatccgcta ctacacctac ctgatcatga acaagggcag gctgttgaag    1440
gcgggacgcc aggtgcgaga gcccggccag gacctggtgg tgctgcccct gtccatcacc    1500
accgacttca tcccttcctt ccgcctggtg gcgtactaca cgctgatcgg tgccagcggc    1560
cagagggagg tggtggccga ctccgtgtgg gtggacgtca aggactcctg cgtgggctcg    1620
ctggtggtaa aaagcggcca gtcagaagac cggcagcctg tacctgggca gcagatgacc    1680
ctgaagatag agggtgacca cggggcccgg gtggtactgg tggccgtgga caagggcgtg    1740
ttcgtgctga ataagaagaa caaactgacg cagagtaaga tctggacgt ggtggagaag    1800 gcagacatcg gctgcacccc gggcagtggg aaggattacg ccggtgtctt ctccgacgca    1860
gggctgacct tcacgagcag cagtggccag cagaccgccc agagggcaga acttcagtgc    1920
ccgcagccag ccgcccgccg acgccgttcc gtgcagctca cggagaagcg aatggacaaa    1980
gtcggcaagt accccaagga gctgcgcaag tgctgcgagg acggcatgcg ggagaacccc    2040
atgaggttct cgtgccagcg ccggacccgt ttcatctccc tgggcgaggc gtgcaagaag    2100
gtcttcctgg actgctgcaa ctacatcaca gagctgcggc ggcagcacgc gcgggccagc    2160
cacctgggcc tggccaggag taacctggat gaggacatca ttgcagaaga gaacatcgtt    2220
tcccgaagtg agttcccaga gagctggctg tggaacgttg aggacttgaa agagccaccg    2280
aaaaatggaa tctctacgaa gctcatgaat atattttga aagactccat caccacgtgg    2340
gagattctgg ctgtcagcat gtcggacaag aaagggatct gtgtggcaga ccccttcgag    2400
gtcacagtaa tgcaggactt cttcatcgac ctgcggctac cctactctgt tgttcgaaac    2460
gagcaggtgg aaatccgagc cgttctctac aattaccggc agaaccaaga gctcaaggtg    2520
agggtggaac tactccacaa tccagccttc tgcagcctgg ccaccaccaa gaggcgtcac    2580
cagcagaccg taaccatccc ccccaagtcc tcgttgtccg ttccatatgt catcgtgccg    2640
ctaaagaccg gcctgcagga agtggaagtc aaggctgccg tctaccatca tttcatcagt    2700
gacggtgtca ggaagtccct gaaggtcgtg ccggaaggaa tcagaatgaa caaaactgtg    2760
gctgttcgca ccctggatcc agaacgcctg ggccgtgaag gagtgcagaa agaggacatc    2820
ccacctgcag acctcagtga ccaagtcccg gacaccgagt ctgagaccag aattctcctg    2880
caagggaccc cagtggccca gatgacagag gatgccgtcg acgcggaacg gctgaagcac    2940
ctcattgtga cccctcggg ctgcggggaa cagaacatga tcggcatgac gcccacggtc    3000
atcgctgtgc attacctgga tgaaacggag cagtgggaga gttcggcct agagaagcgg    3060 caggggggcct tggagctcat caagaagggg tacacccagc agctggcctt cagacaaccc    3120
agctctgcct ttgcggcctt cgtgaaacgg gcacccagca cctggctgac cgcctacgtg    3180
gtcaaggtct tctctctggc tgtcaacctc atcgccatcg actcccaagt cctctgcggg    3240
gctgttaaat ggctgatcct ggagaagcag aagcccgacg gggtcttcca ggaggatgcg    3300
cccgtgatac accaagaaat gattggtgga ttacggaaca caacgagaa agacatggcc    3360 ctcacggcct ttgttctcat ctcgctgcag gaggctaaag atatttgcga ggagcaggtc    3420
aacagcctgc caggcagcat cactaaagca ggagacttcc ttgaagccaa ctacatgaac    3480
ctacagagat cctacactgt ggccattgct ggctatgctc tggcccagat gggcaggctg    3540 aagggggcctc ttcttaacaa atttctgacc acagccaaag ataagaaccg ctgggaggac    3600
```

```
cctggtaagc agctctacaa cgtggaggcc acatcctatg ccctcttggc cctactgcag    3660
ctaaaagact ttgactttgt gcctcccgtc gtgcgttggc tcaatgaaca gagatactac    3720
ggtggtggct atggctctac ccaggccacc ttcatggtgt tccaagcctt ggctcaatac    3780
caaaaggacg cccctgacca ccaggaactg aaccttgatg tgtccctcca actgcccagc    3840
cgcagctcca agatcaccca ccgtatccac tgggaatctg ccagcctcct gcgatcagaa    3900
gagaccaagg aaaatgaggg tttcacagtc acagctgaag gaaaaggcca aggcaccttg    3960
tcggtggtga caatgtacca tgctaaggcc aaagatcaac tcacctgtaa taaattcgac    4020
ctcaaggtca ccataaaacc agcaccggaa acagaaaaga ggcctcagga tgccaagaac    4080
actatgatcc ttgagatctg taccaggtac cggggagacc aggatgccac tatgtctata    4140
ttggacatat ccatgatgac tggctttgct ccagacacag atgacctgaa gcagctggcc    4200
aatggtgttg acagatacat ctccaagtat gagctggaca aagccttctc cgataggaac    4260
accctcatca tctacctgga caaggtctca cactctgagg atgactgtct agctttcaaa    4320
gttcaccaat actttaatgt agagcttatc cagcctggag cagtcaaggt ctacgcctat    4380
tacaacctgg aggaaagctg tacccggttc taccatccgg aaaaggagga tggaaagctg    4440
aacaagctct gccgtgatga actgtgccgc tgtgctgagg agaattgctt catacaaaag    4500
tcggatgaca aggtcaccct ggaagaacgg ctggacaagg cctgtgagcc aggagtggac    4560
tatgtgtaca agacccgact ggtcaaggtt cagctgtcca atgactttga cgagtacatc    4620
atggccattg agcagaccat caagtcaggc tcggatgagg tgcaggttgg acagcagcgc    4680
acgttcatca gccccatcaa gtgcagagaa gccctgaagc tggaggagaa gaaacactac    4740
ctcatgtggg gtctctcctc cgatttctgg ggagagaagc ccaacctcag ctacatcatc    4800
gggaaggaca cttgggtgga gcactggcct gaggaggacg aatgccaaga cgaagagaac    4860
cagaaacaat gccaggacct cggcgccttc accgagagca tggttgtctt tgggtgcccc    4920
aactga                                                               4926
```